(12) United States Patent
Li et al.

(10) Patent No.: US 10,849,531 B2
(45) Date of Patent: Dec. 1, 2020

(54) SYSTEMATIC APPARATUS FOR MOTION SENSOR AND OPTICAL SENSOR BASED CARDIAC ARRHYTHMIA TRIAGE

(71) Applicant: Samsung Electronics Co., Ltd., Suwon-si (KR)

(72) Inventors: Yelei Li, San Jose, CA (US); Matthew Wiggins, San Jose, CA (US)

(73) Assignee: Samsung Electronics Co., Ltd.

( * ) Notice: Subject to any disclaimer, the term of this patent is extended or adjusted under 35 U.S.C. 154(b) by 191 days.

(21) Appl. No.: 16/017,943

(22) Filed: Jun. 25, 2018

(65) Prior Publication Data

US 2019/0313947 A1  Oct. 17, 2019

Related U.S. Application Data

(60) Provisional application No. 62/658,962, filed on Apr. 17, 2018.

(51) Int. Cl.
| | |
|---|---|
| *A61B 5/00* | (2006.01) |
| *A61B 5/021* | (2006.01) |
| *A61B 5/0402* | (2006.01) |
| *A61B 5/024* | (2006.01) |
| *A61B 5/11* | (2006.01) |
| *A61B 5/053* | (2006.01) |
| *A61B 5/06* | (2006.01) |

(52) U.S. Cl.
CPC ............ *A61B 5/1102* (2013.01); *A61B 5/024* (2013.01); *A61B 5/067* (2013.01); *A61B 5/1118* (2013.01); *A61B 5/746* (2013.01); *A61B 2562/0219* (2013.01)

(58) Field of Classification Search
None
See application file for complete search history.

(56) References Cited

U.S. PATENT DOCUMENTS

| | | | |
|---|---|---|---|
| 9,814,406 B2 | 11/2017 | Razavi et al. | |
| 10,492,733 B2 * | 12/2019 | Airaksinen | ............ G16H 50/30 |
| 2018/0000426 A1 | 1/2018 | Li | |
| 2018/0116606 A1 | 5/2018 | Li et al. | |

FOREIGN PATENT DOCUMENTS

| | | |
|---|---|---|
| JP | 4705358 B2 | 6/2011 |
| JP | 6197926 B2 | 9/2017 |
| KR | 10-2010-0065084 A | 6/2010 |
| KR | 10-1659798 B1 | 9/2016 |
| KR | 10-1704491 B1 | 2/2017 |

OTHER PUBLICATIONS

U.S. Appl. No. 15/726,756, filed Oct. 6, 2017, pp. 1-48.

* cited by examiner

*Primary Examiner* — Brian T Gedeon
(74) *Attorney, Agent, or Firm* — Innovation Counsel LLP

(57) ABSTRACT

A method for detecting arrhythmia, including receiving, via at least one motion sensor, channels of raw motion signals for a user; monitoring the channels for motion activity; generating segments from the raw motion signals; determining heartbeat event locations from the generated segments; performing false alarm detection on the raw motion signals and heartbeat event locations to generated refined abnormal candidates.

22 Claims, 16 Drawing Sheets

SYSTEMATIC APPARATUS FOR MOTION SENSOR AND OPTICAL SENSOR BASED CARDIAC ARRHYTHMIA TRIAGE

RELATED APPLICATIONS

This application claims the benefit of the U.S. Provisional Application 62/658,962, filed on Apr. 17, 2018, the disclosure of which is incorporated herein in its entirety by reference. This application incorporates in its entirety by reference U.S. application Ser. Nos. 15/726,756 and 15/370,468.

FIELD OF THE INVENTION

The present disclosure relates to measuring a user's body signals, and more particularly, to a system and method for a generic cardiac arrhythmia triage framework using a motion sensor alone, or in conjunction with other sensors, such as an optical sensor. A system and method of continuous permanent and paroxysmal arrhythmia detection is disclosed, which is an ideal solution for personal electronic device implementation.

BACKGROUND

Conventional beat detection methods are typically used to determine health measurements (e.g., heart rate, respiration rate) from various types of measurement sensors. These measurement sensors measure different types of sensor signals such as, for example, photoplethysmogram (PPG) signals, electrocardiogram (ECG) signals, galvanic skin response (GSR) signals, and bio-impedance signals. An ECG utilizes electrical activity and requires multiple leads positioned at different points on the body. Similarly, PPG may also be problematic for wearable devices due to its relatively high power requirements. However, in a portable, wearable electronic device that monitors biosignals, motions of the user and other sources of noise using motion sensors can make accurate detection of biosignals challenging. It is desirable that a wearable electronic device use a method of monitoring biosignals that has lower power consumption.

SUMMARY

The present inventive concept provides a system and method of continuous permanent and paroxysmal arrhythmia detection, including detecting ballistocardiography (BCG) signals and seismocardiography (SCG) signals.

A method for detecting arrhythmia, comprising: receiving, via at least one motion sensor, channels of raw motion signals for a user; monitoring the channels for motion activity; generating segments from the raw motion signals; determining heartbeat event locations from the generated segments; performing false alarm detection on the raw motion signals and heartbeat event locations to generated refined abnormal candidates.

An electronic device, comprising: at least one motion sensor configured to detect raw motion signals for a user and output the raw motion signals as individual channels; a processor configured to: monitor the channels for motion activity; generate segments from the raw motion signals; determine heartbeat event locations from the generated segments; and perform false alarm detection on the raw motion signals and heartbeat event locations to generated refined abnormal candidate; and a display configured to display at least one of the one or more of the health information.

These and other advantages, aspects and novel features of the present disclosure, as well as details of an illustrated embodiment thereof, will be more fully understood from the following description and drawings.

BRIEF DESCRIPTION OF THE DRAWING

These and other features and advantages of the present disclosure will be appreciated and understood with reference to the specification, claims, and appended drawings wherein:

DETAILED DESCRIPTION

Figure 1:
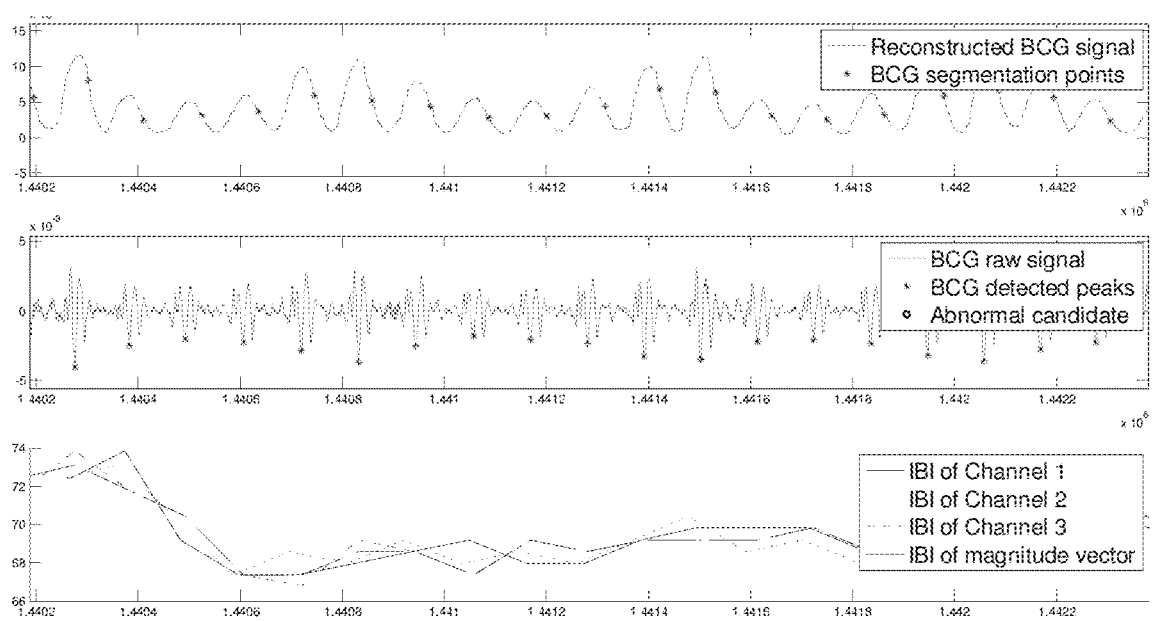
FIG. 1 depicts information extraction from motion sensor signals according to an embodiment of the present inventive concept.

Various example embodiments of the disclosure will be described in detail with reference to the accompanying drawings such that they can be made and used by those skilled in the art.

Various aspects of the present disclosure may be embodied in many different forms and should not be construed as being limited to the example embodiments set forth herein. Rather, these example embodiments of the disclosure are provided so that this disclosure will be thorough and complete and will convey various aspects of the disclosure to those skilled in the art.

The detailed description set forth below is intended as a description of various example embodiments of a system and method for real-time heartbeat events detection using a low-power motion sensor. Usage of low-power motion sensor for real-time heartbeat events detection may be described in more detail in the U.S. application Ser. No. 15/726,756.

The detailed description set forth below in connection with the appended drawing is intended as a description of exemplary embodiments of a system and method for motion Sensor and optical sensor based cardiac arrhythmia triage, provided in accordance with the present inventive concept and is not intended to represent the only forms in which the present inventive concept may be constructed or utilized. The description sets forth the features of the present inventive concept in connection with the illustrated embodiments. It is to be understood, however, that the same or equivalent functions and structures may be accomplished by different embodiments that are also intended to be encompassed within the spirit and scope of the present inventive concept. As denoted elsewhere herein, like element numbers are intended to indicate like elements or features.

Heartbeats of a user may be detected by a motion sensor(s), particularly when the user is stationary, or nearly so. Heartbeats of a user can be characterized by the intervals between individual beats, or the inter-beat interval (IBI), which is defined as follows:

$$IBI(i)=\text{beat\_timestamp}(i+1)-\text{beat\_timestamp}(i)$$

Furthermore, instantaneous heart rate (BPM; aka instantaneous HR) can be derived from IBI (where the units of measurement for IBI is in seconds):

$$\text{Instantaneous HR}=60/IBI$$

By applying a normal heart rate change threshold on Instantaneous HR data, abnormal heart rate change can be identified for a given user. Usually, abnormal heart rate implies several arrhythmia types (Atrial Fibrillation, Premature Ventricular Contraction, etc.); moreover, instantaneous heart rate distribution over a long time window can further help to identify abnormal patterns such as bigeminy, trigeminy, etc.

Ballistocardiography (BCG) measures body acceleration caused by cardiac output as well as respiration. BCG contains multiple peak events during one heartbeat. These peaks can be categorized into three major groups: pre-systolic, systolic, and diastolic. Systolic waves may correspond to QRS complexes in ECG signal, and they may be a salient features of BCG. BCG signals, however, may also include a wide variety of peaks due to frequency position (orientation) changes as well as level of stability of the measured subject. In wearable applications, it may be possible to take BCG measurements using one or more motion sensors, such as, for example, an accelerometer; however, it may be useful to take into account the movements of the user wearing the user-wearable device as these movements may act as noise to the BCG measurements. This may be especially true if the user-wearable device is worn on a user's wrist, which may be prone to sudden and unexpected motions.

Accordingly, various embodiments of the disclosure may describe a system for detecting heartbeat events using a motion sensor using one or more of combined channel selection, cross-correlation, and a probability hybrid network. By using a low-power, low-noise motion sensor to detect heartbeat events, the battery life of the device may be significantly extended. Additionally, the precision of the beat locations may be increased.

Various embodiments described below may require less power and yet provide higher precision compared to, for example, an optical approach such as a PPG device, and, yet, when the user is stationary, may prove to be more flexible compared to an ECG device since the disclosed algorithm may enable heartbeat event detection at various body locations or even remote locations without having to have multiple leads positioned at different points of the user's body.

In general, beat detection algorithms may introduce false/miss detections of heart beat events, and a threshold-based abnormal detection may produce false alarms. In order to reduce or eliminate false alarms, a post-correction method in an embodiment of the present inventive concept is proposed to refine abnormal candidates.

1. Channel Combination—Stage 1 Screening

Figure 3A:
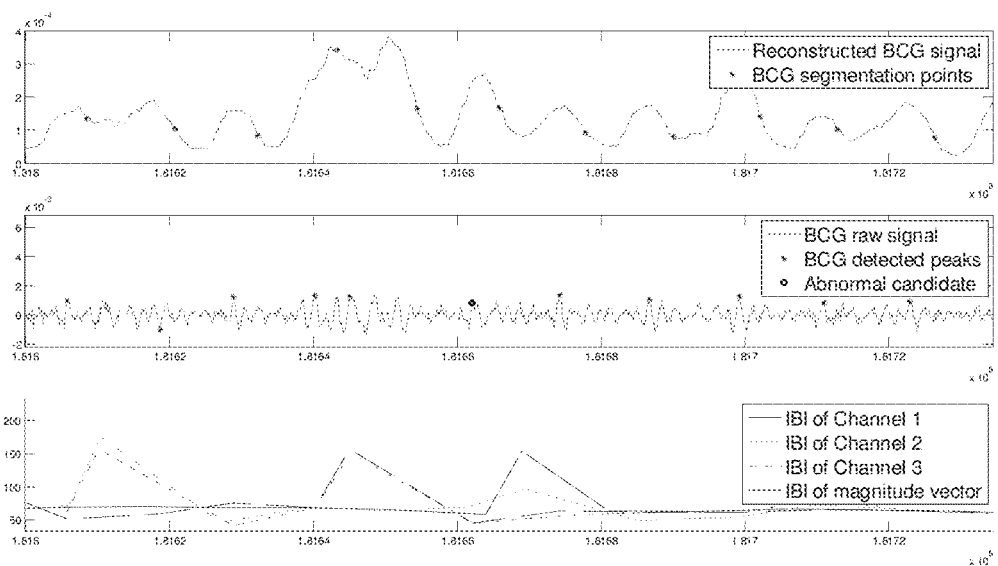
FIGS. 3A and 3B depicts IBI trends comparison for arrhythmia and artifact segments according to an embodiment of the present inventive concept.

In an example embodiment, a 3-axial accelerometer is used to measure cardiac signals with BCG. Heart beat event locations are computed on all 3 channels, as well as the magnitude vector signal, for example as shown in FIG. 3A. For cardiac arrhythmia such as Atrial Fibrillation (A-Fib), BCG J-peak complex is considered identical, and therefore all channels should have the same heart rate change trend without any triggering any reset flag. If all combined channel information is identical, there is a high probability that the detected candidate is an abnormal event. However, this approach does not apply to arrhythmia such as premature ventricular contractions (PVC), since the cardiac function during anomaly onset is different, and different J peak complex is expected. In this case, additional steps have to be taken.

2. Template Matching

In the use case of sleep, the user will usually keep the same sleep posture for a long period; in this case, there could be consistent BCG morphological feature until user changes posture. Once an abnormal event is detected as the candidate is excluded from stage 1 screening, template matching mechanism can be applied and used to identify identical abnormal morphological feature. In FIG. 3A, a first abnormal event is detected and motion sensor channels show a different change trend between the channels, so the candidate is not considered a high confidence anomaly event from stage 1; the first event will be stored into buffer as a template for matching purpose; as a second abnormal event comes in (again, this second candidate should not satisfy stage 1 screening), it will be compared with abnormal beats in the buffer. If both have high similarity, they are considered to be part of the same cluster and, with a higher probability as abnormal heart beats; as the number of beats in the cluster increases, the confidence of a given cluster of beats as abnormal heart events gets higher. Moreover, similarity output (described in more detail in U.S. application Ser. No. 15/726,756) can be used as morphological feature for matching purposes.

3. Morphological Analysis

Arrhythmias are also evidenced in the BCG signal morphology. This can be seen in the relative amplitude of adjacent SCG/BCG J-peaks on the different channels (e.g., in bigeminy, the primary pulse ejects more blood, having a generally larger amplitude than the secondary abnormal beat) and/or morphology of the reflections due to this different stroke volume and timing relative to the initial pulse. In an embodiment of the present inventive concept, using these morphology features in cooperation with the other features mentioned above can be used for the recognition and diagnosis of the presence of arrhythmias. Moreover, morphological features can be extracted using approaches such as time-frequency analysis, autoencoder, convolutional network, etc. Features is further used to train supervised models with pre-annotated labels or used in unsupervised clustering.

4. Noise Identification

Figure 2:
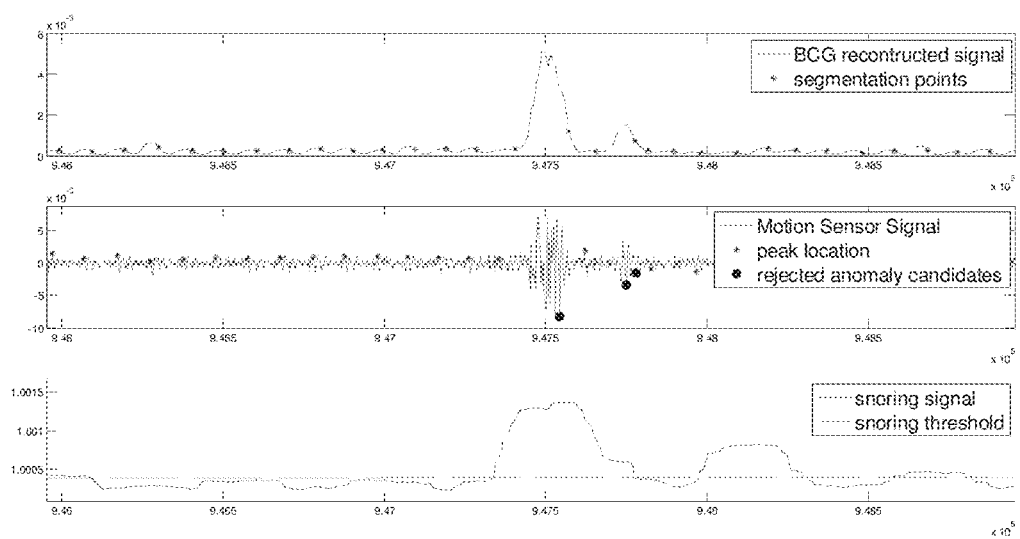
FIG. 2 depicts BCG segment from snoring events according to an embodiment of the present inventive concept.

In many use cases, environmental noises or artifacts may introduce much noise and heavily affect beat detection results. It is important to identify and mask out these noise segments. In one example, a user uses the device for arrhythmia detection during sleep. Events such as snoring or non-heartbeat motions may be excluded. Referring to U.S. application Ser. No. 15/370,468, such noise events are able to be identified, and the majority of abnormal candidates caused by such sources can be removed, i.e. the abnormal candidates can be refined by removing false abnormal candidates. For example, snoring detection may be accomplished by setting a desired frequency band greater than a desired threshold (since a snoring signal frequency is generally greater than 6 Hz); an embodiment may apply an adaptive frequency threshold to detect a snoring event. The adaptive frequency threshold may be varied, for example, for an individual to better detect the snoring signals. The snoring signals may vary in frequency from one individual to another. In another example, an embodiment may use a hold-off parameter to prevent false detections within a single event. In another example, an embodiment may determine one or more parameters such as energy, entropy, and a periodicity rate to detect whether a snoring event occurs in a given time window (e.g., 20 seconds). As illustrated in FIG. 2, black solid dots in the middle plot represent anomaly candidates from stage 1 screening, according to the bottom snoring detection plot, these events happen during a snoring period and the anomaly intervals are, with high probability, caused by snoring movements, and therefore these candidates will be removed from further analysis.

Signal quality is critical in arrhythmia detection applications: according to previous methodology, in a low signal quality period, more reset flags are presented which re-initializes beat localization. However, several types of cardiac arrhythmia would produce different BCG morphological features and cause inconsistent morphology; in this case, many reset flags would also be presented, undesirably re-initializing beat localization. In order to distinguish arrhythmia-caused beat detection reset with ones caused by low signal quality, several options are disclosed below.

1. Signal Quality Assessment Using Reconstructed BCG Signal

This method uses reconstructed BCG signal to determine if the signal quality caused frequent beat detection reset.

2. Combinational Analysis Across Multiple Channels

Figure 3B:
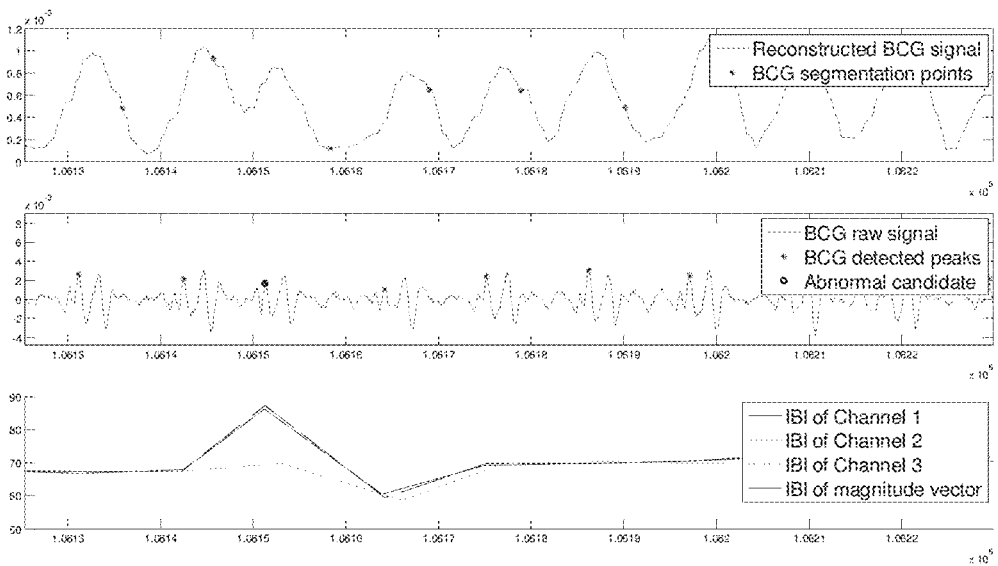

When the 3-axial accelerometer is used to measure the BCG signal, beat detection can be applied on all 3 channels as well as the magnitude vector of the 3 channels. FIGS. 3A and 3B show two examples of using combined channel information for candidate refinement: In FIG. 3A, IBI of 4 channels in a given window show different trends (i.e., heart rate change in some channels are positive while others are negative) whereas in FIG. 3B, IBI of all channels are very consistent. In this example, the abnormal candidate in FIG. 3A is caused by artifacts or noise whereas the candidate in FIG. 3B is a true positive abnormal beat. Moreover, reconstructed BCG signal quality can be quantified.

For the use case of continuous arrhythmia monitoring, in addition to single abnormal event detection, it is also important to identify onset and offset of arrhythmia event periods. For example, A-Fib burden (the amount of time spent in A-Fib) is a very critical index for assessing a user's A-Fib condition evolution, and may be calculated by the processor in the user-wearable device (described in more detail below). Moreover, combining abnormal candidates' location information over a long time window can help to identify arrhythmia type and increase detection confidence: in one example, the IBIs before and after abnormal beats over a given time period will be collected and the IBI distribution will be calculated; the distribution is then compared with an empirical model/distribution of arrhythmia types and the likelihood of a given distribution is quantified. In one embodiment, a logistic regression model with soft-max activation function is used to quantify the likelihood of IBI distribution with pre-set empirical distribution samples.

In the A-Fib detection example, a pre-set threshold can be used to determine A-fib onset and offset locations. If the number of abnormal IBI candidates of a given time window is above the empirical threshold, the beginning of the time window is considered as an onset of the A-Fib event, and the offset can be set as when the number of abnormal IBIs is below the threshold or where no candidates are presented.

Motion sensor-based arrhythmia detection is an ideal solution under long-period low motion circumstances such as sleep, spot-checking measurement, or napping. A BCG/SCG signal from a motion sensor can contain precious cardiac information comparable to an ECG signal; moreover, ultra-low power consumption of BCG/SCG detection can significantly extend battery life of, for example, a portable and wearable electronic device monitoring biosignals.

In an embodiment of the present inventive concept using only a single motion sensor, multiple use cases are disclosed below.

1. Wrist-Band

In this example, a proposed algorithm/apparatus can be implemented into wearable devices such as, for example, Samsung Gear S3. The wearable device detects a user's activity and triggers arrhythmia monitoring under low motion stage. The wearable device continuously collects BCG signals while being worn on the user's wrist, simulate arrhythmia computational block, and logs ongoing events.

2. Remote Monitoring

Figure 4:
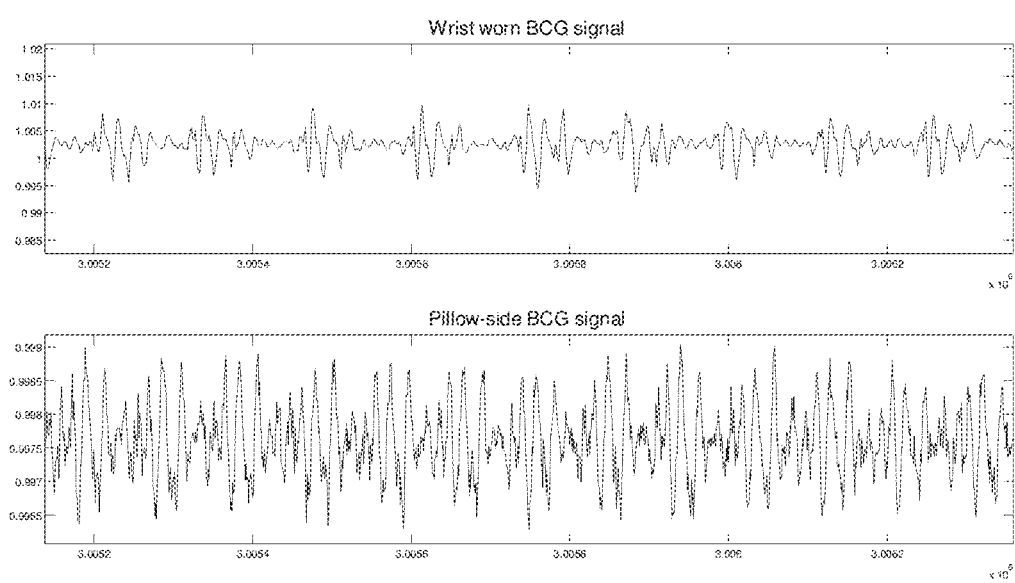
FIG. 4 depicts BCG signals measured from different locations according to an embodiment of the present inventive concept.

Unlike other measurement methods employing such sensors as optical sensors or ECG, motion sensor-based measurement provides very flexible options within the range of body vibration. With a low noise density motion sensor, BCG signals are able to be collected even when the sensor is off of a user's body, e.g., not being worn. In one example, a measurement device (such as a smart watch, mobile phone, etc.) is put beside a user's pillow to the far side of a sleeping partner; in another example, measurement device is attached to a user's pajamas. FIG. 4 shows magnitude vector signals of two measurement use cases.

3. Spot Check Mode

Figure 5:
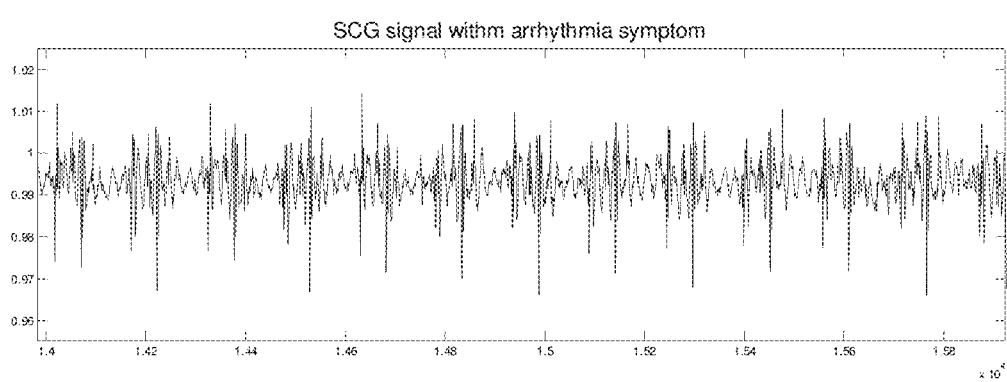
FIG. 5 depicts raw SCG segment with cardiac arrhythmia events according to an embodiment of the present inventive concept.

Spot check mode is defined as when a user actively triggers measurement, and may keep still while data is collecting. In one example, a user may feel symptoms due to arrhythmia and place a mobile phone/smart watch on his/her chest to measure a strong heart sound through SCG. FIG. 5 depicts such an example of a segment of arrhythmia onset, where a signal is acquired by the user placing his/her wrist-based device on the left side of the chest.

As motion sensors for BCG/SCG measurement are sensitive to movement artifacts, they are currently not robust enough alone to do continuous daytime arrhythmia monitoring. A motion sensor may be combined with an optical sensor in a combined solution to solve this issue. Motion sensors have the characteristics of: low power consumption allowing for continuous monitoring, heart beat location (J peak), low SNR, but are sensitive to motion, and have inconsistent morphology. Optical sensors have the characteristics of: consistent morphology, better motion resistance, but are power hungry, and lack salient feature.

In embodiments of the present inventive concept, at least one optical sensor can be used as an additional sensor for arrhythmia detection via PPG signal while under motion, or as a reinforcement module for more accurate detection.

Figure 6:
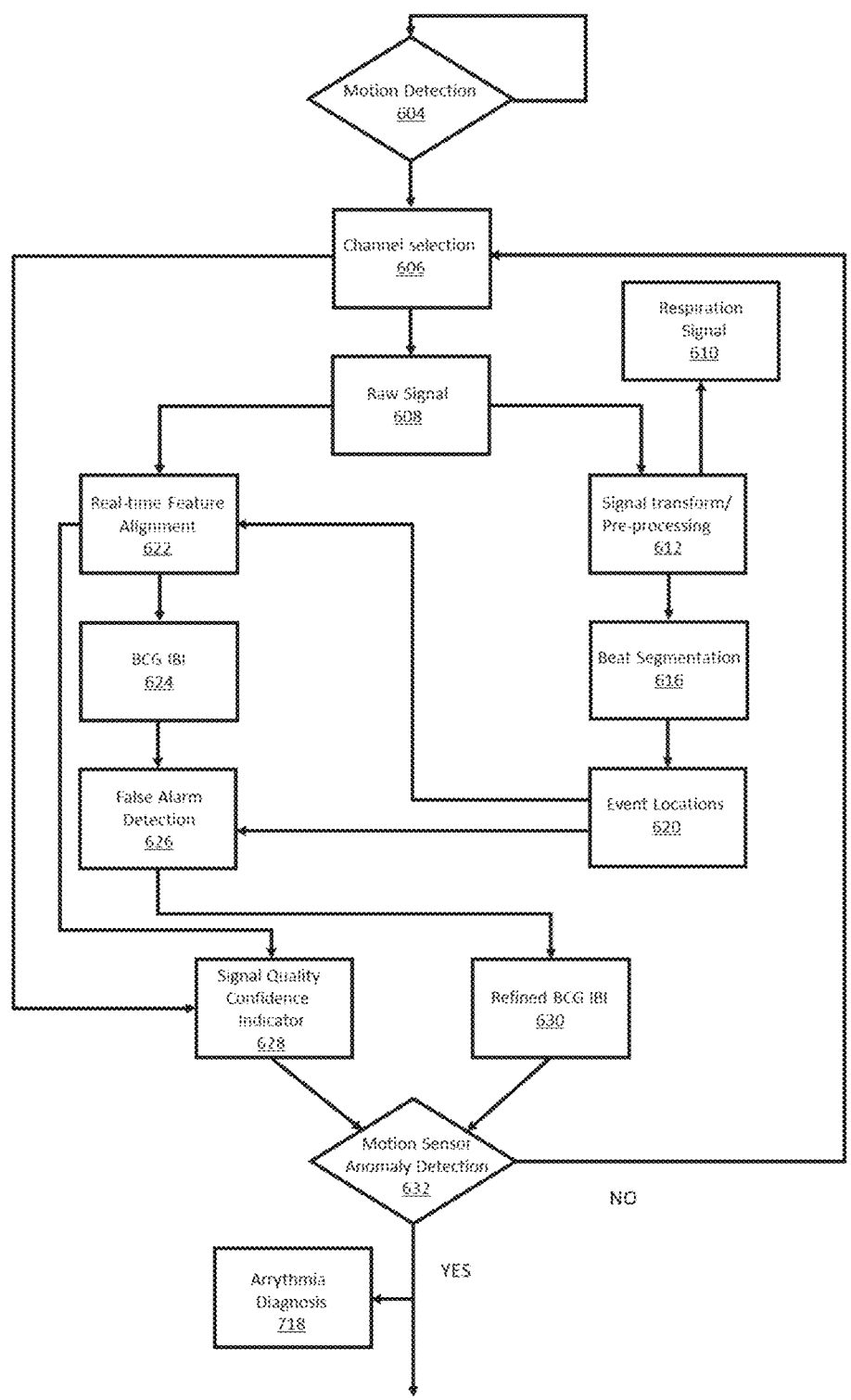
FIG. 6 depicts an arrhythmia triage flowchart according to an embodiment of the present inventive concept.
Figure 7:
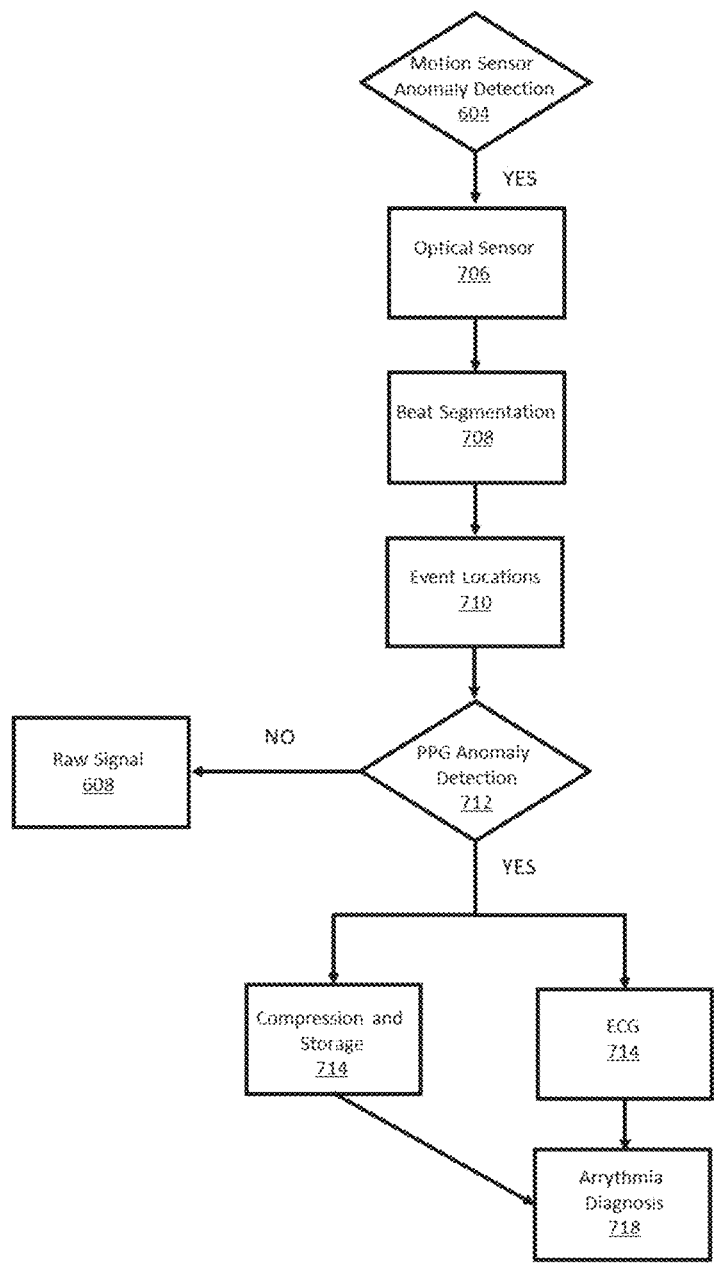
FIG. 7 depicts an arrhythmia triage flowchart according to an embodiment of the present inventive concept.

In one embodiment, a wrist-based device contains at least one of each of a motion sensor, optical sensor and ECG sensor. The motion sensor is continuously active to monitor activity level and measure a BCG signal. All abnormal segments (as shown in FIG. 3) are recorded, and the Motion Sensor Anomaly Detection Block monitors statistical distribution of abnormal IBIs (inter-beat interval). Once the value reaches a significant threshold, the optical sensor will be triggered to confirm abnormal observations. PPG IBIs and morphological information will be combined with BCG based information, with PPG and BCG running simultaneously, and if both IBIs are within abnormal ratios for a predetermined time period, arrhythmia detection is considered positive and passed to PPG and Motion Sensor Anomaly Detection for statistical quantification. If arrhythmia events are confirmed, abnormal PPG and BCG segments will be processed through the compression block and stored in device storage module. The compression block can be implemented to be using—but not limited to—wavelet compression, down-sample, etc. In the case that the user is active, the BCG signal is used for initial screening, and when motion is present or detection confidence is low, the optical sensor will be triggered as primary detection source. If an anomaly event is detected—that is, if both motion and optical sensor confirm arrhythmia symptoms—the system will send a notification to the user recommending that the user then engage in a spot check mode using ECG sensor, for clinical confirmation. In this case, only the ECG raw signal will be stored for further use. FIGS. 6 and 7 depicts the above-described process.

Figure 10:
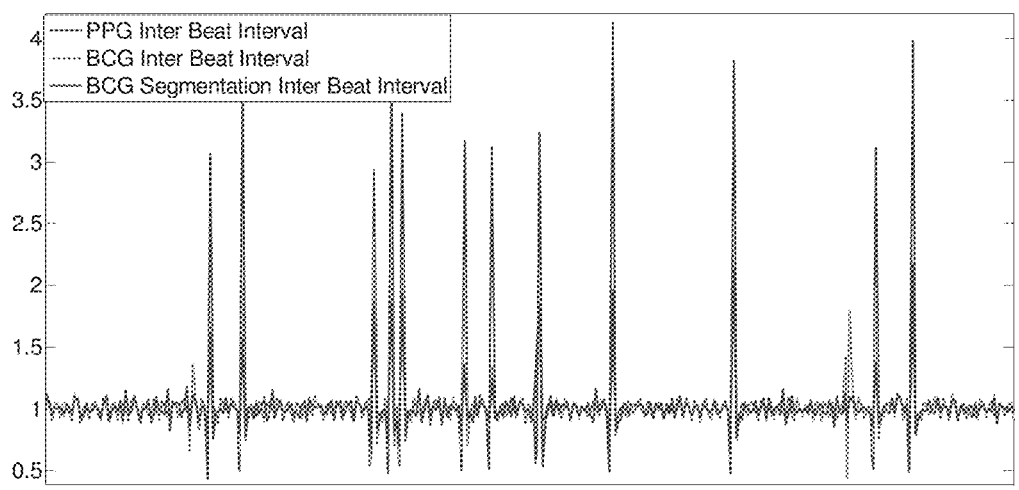
FIG. 10 depicts false alarm detection results according to an embodiment of the present inventive concept.

Because a motion sensor signal is noisy, it might introduce a false alarm (false beat detection) at the BCG diagnosis stage. Additional embodiments of the present inventive concept solve this issue, where a False Alarm Detection block combines raw beat detection locations (segmentation locations in FIGS. 3A and 3B) and refined locations (refined heart beats in FIGS. 3A and 3B) to mask out a false arrhythmia detection. FIG. 10 illustrates the results of such false alarm masking.

In some embodiments of the present inventive concept, if ECG spot check is not feasible (e.g., the user is sleeping), raw BCG and PPG signals are stored for further diagnosis. For example, in the Compression block in FIG. 7, raw BCG and PPG signal may be stored.

In some embodiments, a user's electronic health record (EHR), biometric information and other user inputs are imported into the wearable device. Historical arrhythmia records are used to help to increase detection confidence as well as distinguish between asymptomatic appearance of arrhythmia and obvious symptoms caused by arrhythmia.

The embodiments described can also be applied for exercise stress tests. Exercise is a stressful situation where at the beginning or end of exercise arrhythmia might occur, and it is therefore valuable to evaluate a user's heart rate response to exertion and further help understand cardiac condition.

Moreover, embodiments may be helpful for a user's lifestyle improvement. Arrhythmia incidental events can be triggered by bad lifestyle such as caffeine/alcohol consumption, stressful mentality or lack of sleep. Continuous arrhythmia monitoring will clearly show their impacts.

Cardiac arrhythmias are known as common issues in populations with sleep disease such as obstructive sleep apnea (OSA), although the mechanism link between them is unknown. Potentially, embodiments of the present inventive concept can help users and their doctors have a broad understanding of the user's arrhythmia development correlated with sleep condition and for better/more efficient treatment.

Another feature of the present inventive concept is a median filter for AFib feature refinement.

Figure 15:
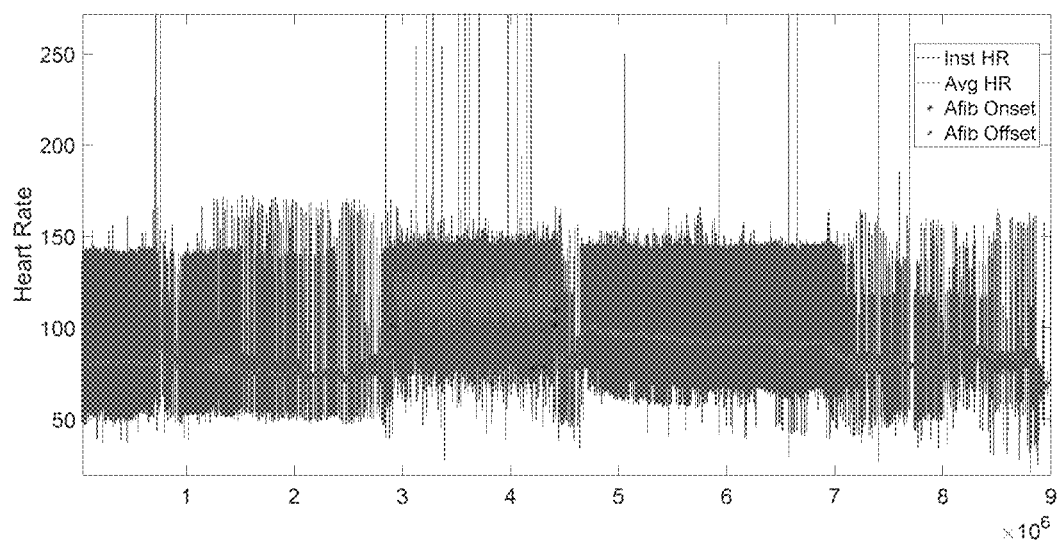
FIG. 15 depicts application of a median filter to instantaneous heart rate according to an embodiment of the present inventive concept.
Figure 16:
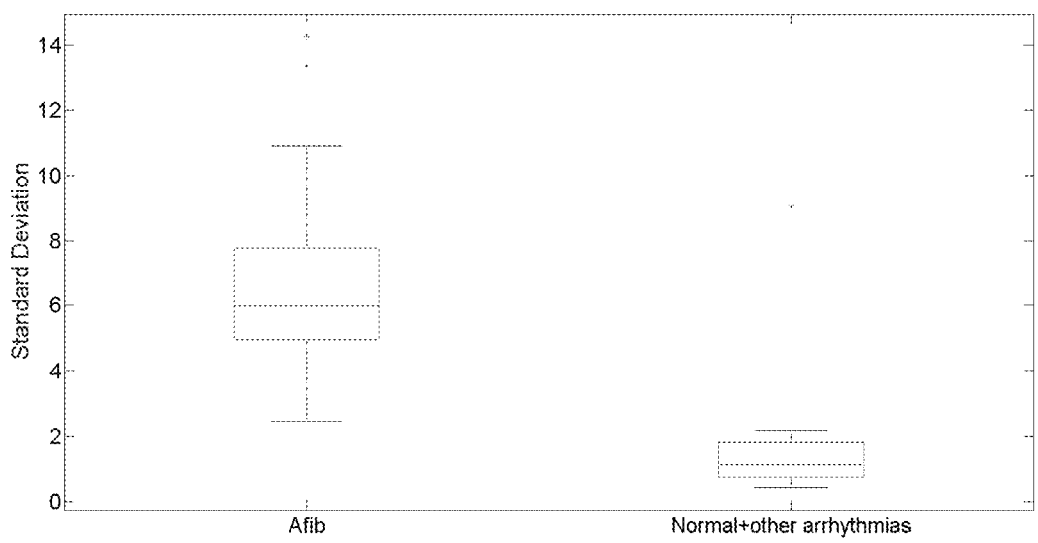
FIG. 16 depicts standard deviation of a signal plotted in FIG. 15 according to an embodiment of the present inventive concept.

One of the most salient feature to identify AFib is the irregularity and randomness of heartbeat inter-beat interval (IBI) rhythm. In the instantaneous heart rate plot (HR=60/IBI) of FIG. 15, the instantaneous HR (Inst HR) distribution looks very similar to other arrhythmia such as premature ventricular contraction (PVC). However, most other arrhythmias with irregular IBI are not randomly distributed. The average HR (Avg HR) from FIG. 15 shows a 20th order median filter filtered HR. It is very clear that the AFib HR (from around 3 to 4.5 on the x-axis) is distinguishable from other periods of the signal. The AFib HR, run through the median filter, has a much higher standard deviation from other periods of the signal, as shown in FIG. 16.

A median filter or like filter may be used for feature extraction. The median filter may be of Nth order, where N is a natural number empirical value based on, for example, sensing rate, heart rate range and other biometric parameters (for example, if the raw signal sensing rate is 100 Hz, and the average individual's sleeping heart rate is 50-150 BPM, then N may be set to 20). The order of the median filter may represent how many heartrate points are sampled to find the median value in the moving window of the median filter.

Furthermore, in one embodiment, the signal may be run through more than one median filter for better results. For example, the Instantaneous HR may be fed into at least 2 median filters: one has an odd value as the order and the other one has an even value for the order (e.g a pair median filters with order of 20 and 21). The filtered HRs may be compared to each other sample by sample: if the filtered HR from both filters are within a certain range (e.g. HR are within 5 bpm or HR difference are within 5%), the given period is considered a normal/AFib candidate; if the difference is out of the predetermined range, this period will be excluded from further calculation and can be considered as artifacts or other arrhythmia types. In one embodiment, the output of the filtering can be used to further identify arrhythmia such as bigeminy, trigiminy, etc.

The advantages to use median filter batches (particularly in the pre-processing step) is that it can help distinguish Afib from artifacts and other arrhythmias. This proposed approach can be applied to any physiological signal where heartbeats can be extracted. Moreover, for low SNR signals such as BCG, the median filters can significantly improve the accuracy of IBI without dramatically decreasing final performance.

Figure 11:
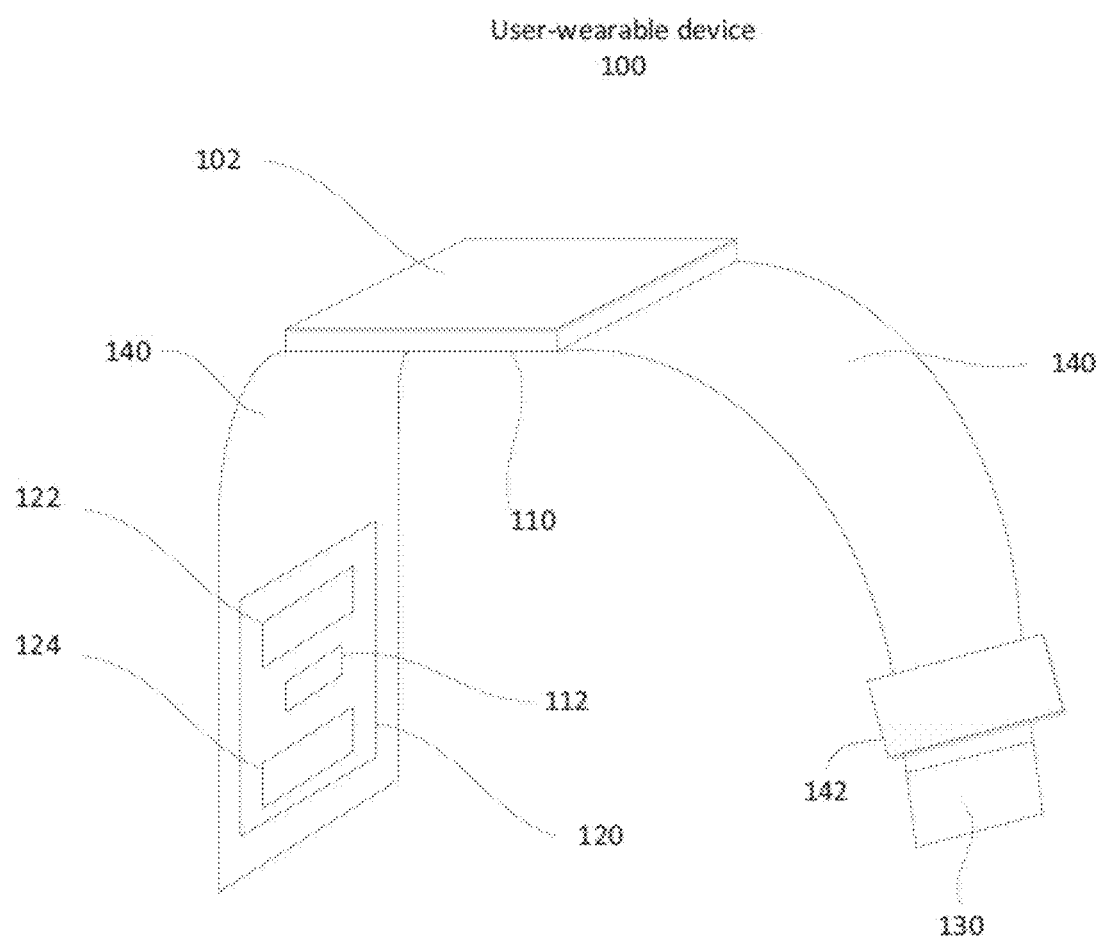
FIG. 11 is a diagram illustrating an electronic device, in accordance with various example aspects of the inventive concept.

FIG. 11 is a diagram illustrating an electronic device in accordance with an embodiment of the present disclosure. Referring to FIG. 11, an electronic device, such as the user-wearable device 100, has a display 102, control block 110, the processor 112, a sensor module 120, a battery 130, a band 140, and a clasp 142. The sensor module 120 may include sensors 122 and 124. The control block 110, the processor 200 (FIG. 12), and/or the processor 112 may also be referred to as a diagnostic processor, and may be able to execute instructions. Accordingly, a diagnostic processor may comprise, for example, a digital signal processor, a controller, a use specific processor, a general processor, and so on. At times, for ease of description, a diagnostic processor may also generally refer to a combination of various hardware.

Although the user-wearable device 100 can be worn on a wrist, various embodiments of the disclosure need not be so limited. The user-wearable device 100 may also be designed to be worn on other parts of the body, such as, for example, on an arm (around the forearm, the elbow, or the upper arm), on a leg, on the chest, on the head like a headband, on the throat like a "choker," and on an ear. The user-wearable device 100 may be able to communicate with other electronic devices such as, for example, a smartphone, a laptop, or various medical devices at a hospital or a doctor's office. This will be described in more detail with respect to FIG. 3.

The display 102 may output monitored physiological signals from the user's body for viewing by the user and/or others. The signals being monitored may be referred to as biosignals or biometric data. The monitored signals may be, for example, heart (pulse) rate, pulse morphology (shape), pulse spacing (inter-beat intervals), respiration (breathing) rate, and blood pressure. The display 102 may also output instructions to the user or others in the use of the user-wearable device 100 or use of other measurement devices, as well as status and diagnostic results, for example.

The control block 110 can receive the monitored signals via a sensor in the sensor module 120. The sensor module 120 may include, for example, the sensors 122 and 124 that may acquire signals from the user's wrist when the user-wearable device 100 is worn by a user, as well as provide other information that may indicate the user's body position, motion, and the like. The sensor 122 and/or 124 may be, for example, an accelerometer, a gyroscope, piezoelectric device, an optical sensor such as, for example, a camera, a sensor using sonic frequencies, and the like. An accelerometer may be, for example, a hardware electromechanical device measuring acceleration on three axes. The processor 112 may control the sensors 122 and 124, and may also process the signals monitored by the sensors 122 and 124. Various embodiments of the disclosure may have the control block 110 also perform the functions of the processor 112. Various embodiments of the disclosure may also have different number of sensors.

The sensor 122 may be used, for example, to monitor motion. The sensor 124 may be similar to the sensor 122 or a different type of sensor such as, for example, a thermometer for taking the user's temperature. Various embodiments of the disclosure may include different numbers of sensor modules. For example, some embodiments may only have one sensor module, while other embodiments may have 2 or more sensor modules.

The battery 130 is configured to provide power for the user-wearable device 100. The battery 130 may be charged using a wired charging system or a wireless charging system. The band 140 may be wrapped around a wrist and the user-wearable device 100 may be held on the wrist by using the clasp 142.

Figure 12:
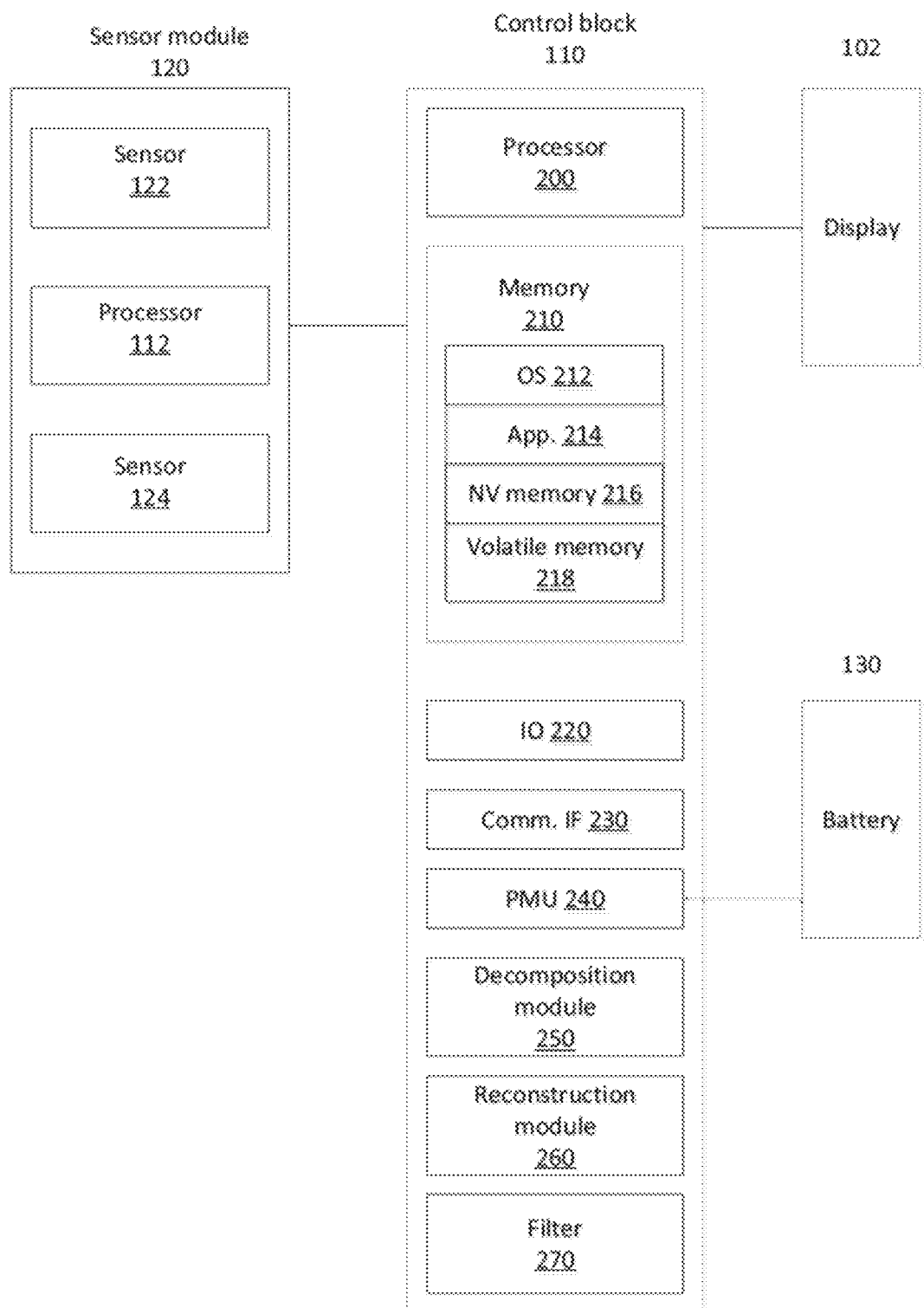
FIG. 12 is a high-level block diagram of an electronic device, in accordance with various example aspects of the inventive concept.
Figure 13:
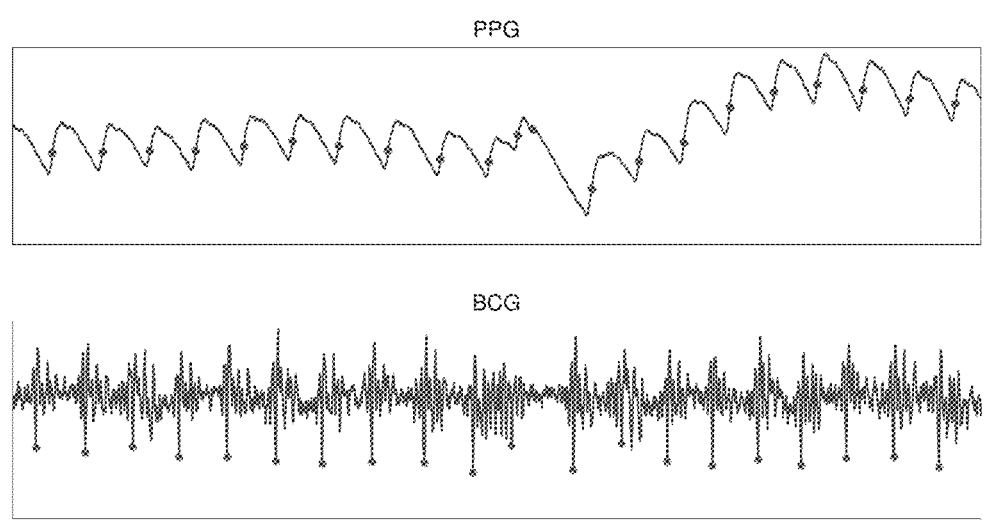
FIG. 13 depicts PPG and BCG signals from a wearable device according to an embodiment of the present inventive concept.
Figure 14:
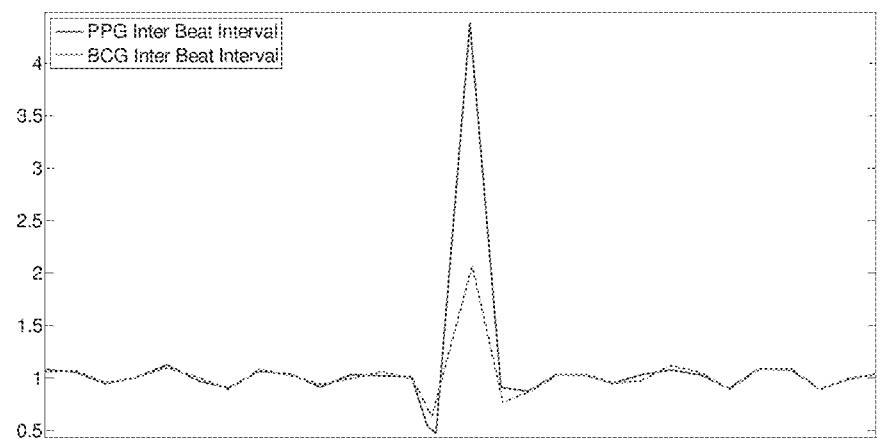
FIG. 14 depicts interbeat interval ratio of detected beats according to an embodiment of the present inventive concept.

FIG. 12 is a high-level block diagram of an electronic device in accordance with an embodiment of the present disclosure. Referring to FIG. 2, there is shown the display 102, the control block 110, the sensor module 120, and the battery 130. Output to the display 102 can be controlled, for example, by the control block 110. The display 102 may also include input devices (not shown) such as, for example, buttons, dials, touch sensitive screen, and microphone.

The control block 110 may include a processor 200, memory 210, an input/output (IO) interface 220, a communication interface 230, a power management unit (PMU) 240, a decomposition module 250, a reconstruction module 260, and a filter 270. While the control block 110 is described as including these various devices, other embodiments may use other architectures where the different functionalities are grouped differently. For example, the grouping may be in different integrated circuit chips. Or the grouping may be combining different devices such as the IO interface 220 and the communication interface 230 together, or the decomposition module 250 and the reconstruction module 260 together.

The processor 200 may control operation of the sensor module 120 as well as receive monitored signals from the sensor module 120. The processor 200 may control the user-wearable device 100, including processing the monitored signals from the sensor module 120, displaying the processed signals on the display 102, receiving input from the display 102, interfacing with various devices via the IO interface 220 or the communication interface 230 by executing instructions in the memory 210. The IO interface 220 may be used by the processor 200 to interface with the display 102.

The processor 112 may operate using different architectures in different embodiments. For example, the processor 112 may use the memory 210 to store instructions to execute, or the processor 112 may have its own memory (not shown) for its instructions. The processor 112 may also have other functionalities found in the control block 110. Although some embodiments have separate processors 200 and 112, the various embodiments need not be limited so. There may be one control block 110 that controls the functionality of the user-wearable device 100, or there may be multiple processors for the user-wearable device 100.

The memory 210 may include non-volatile memory 216 and volatile memory 218. The operating system and applications may be stored in the non-volatile memory 216. Various embodiments of the disclosure may use different memory architectures that are design and or implementation dependent.

The communication interface 230, which comprises a transceiver, may allow the user-wearable device 100 to communicate with other devices via, for example, a wired or wireless protocol such as USB, Bluetooth, Near Field Communication (NFC), and WiFi. The PMU 240 may control receiving power from an outside source, charging the battery 130, as well as allocation of power to the different parts of the user-wearable device 100.

The decomposition module 250 may function to decompose, for example, an input signal such as a BCG signal to multiple frequency bands using time-frequency transforms. The reconstruction module 260 may function to reconstruct, for example, the decomposed signals from the decomposition module 250 to refine and access desired components of the original signal such as the BCG signal. Accordingly, the functions of the decomposition module 250 and the reconstruction module 260 may be performed by, for example, a processor and/or specialized hardware devices. The hardware devices may be off-the-shelf or designed as, for example, an integrated circuit, ASIC, FPGA, etc. For convenience, the decomposition module 250 and the reconstruction module 260 may together be referred to as a transform module. Decomposition and reconstruction of a signal is explained in more detail in the U.S. application Ser. No. 14/928,072. The filter 270 may be used to select specific frequencies from a signal. For example, the filter 270 may be a low-pass filter, a bandpass filter, a high-pass filter, etc., that may attenuate certain frequencies.

FIG. 6 is an example flow chart for processing an input signal in accordance with an embodiment of the present disclosure. Referring to FIG. 6, there is shown the flow chart that describes detecting abnormal candidates in a present example system. The signal to be processed may be received from a wearable device such as, for example, a user-wearable device 100. The user-wearable device 100 may detect the biosignals via the sensor module 120.

At 604, a sensor such as an accelerometer on the sensor module 120 may monitor/detect user motion. While some biosignals may not be affected by user motion, other monitored biosignals provide better signals when the user is substantially stationary. For example, BCG signals may provide more reliable signals when the user is substantially stationary. Accordingly, when a BCG signal is desired, if user motion is at or above a pre-determined threshold level, the process may loop back to 604. When the user motion is below the pre-determined threshold, the biosignal from the sensor may be accepted for processing, and the process proceeds to 606. It should be noted that monitoring motion at 604 may be optional for some embodiments of the present disclosure.

At 606, for those embodiments where there are multiple channels to choose from, the present example system may select a channel or channel(s) to determine a desired signal candidate. For example, if measurement sensors such as an accelerometer and a gyrometer provide BCG signals, the channel candidates may include outputs for each of the three axes of the accelerometer, a magnitude of the accelerometer, and multiple outputs for the gyrometer for a multitude of channels from which to pick a channel. However, various embodiments of the disclosure need not be so limited. According to one embodiment, the present example system may further combine channels as signal fusion for signal quality enhancement purposes to form a new channel, further increasing the number of channels. The present example system may select a channel based on, for example, one or more of recurrence rate analysis, determinism of dominate (or dominant) frequency in frequency spectrum, and entropy analysis. For example, when using spectral analysis for BCG channel selection, a higher power ratio of dominant frequency component can indicate better determinism of measured signal as well as fewer artifacts. In another example, if the signal from the channel has dipped below a threshold for signal acceptability, another channel is selected. Various embodiments may also have channel selection as an option. For example, if there is only one channel input, then there is no need for channel selection.

At 608, the present example system receives raw signal from the selected channel(s) of the sensor.

At 612, the present example system pre-processes the raw signal (from 608) from the selected channel or directly from the measurement sensor, depending on whether there is a channel selection process at 606. For example, the present example system may pre-process the BCG signals to remove respiration artifacts and high frequency disturbances by using techniques such as, for example, time-frequency processing technique and/or a time-domain processing technique. Time-frequency processing technique includes, among others, wavelet coefficient reconstruction, and time-domain processing technique includes, among others, bandpass filtering.

An embodiment may filter raw BCG signal using a bandpass filter with a desired pass frequency band of, for example, substantially 0.5-3.5 Hz. The bandpass filtering may be via the bandpass filter 270, or performed via digital signal processing using one or more diagnostic processors such as, for example, the processor 112 or the CPU 200. Pre-processing at 612 may also be optional if the signal from the user is determined to be a relatively clean signal.

The pre-processed signals are generated as, for example, bandpass filtered signals. In other embodiments, the present example system may decompose the raw BCG signals into frequency bands. For example, a BCG signal may be decomposed with a sampling rate of 100 Hz using 5-level Daubechies5 wavelet. The wavelet coefficients from the second to the fifth frequency bands may be considered to carry a majority of the heart beat information. Very low frequency (VLF) bands may be considered as respiration signals. It should be noted that the mother wavelet and decomposition settings (e.g., number of decomposition levels) may be adjusted to achieve similar results without deviating from the scope of the present disclosure.

The present example system may then use wavelet coefficient reconstruction to reconstruct the decomposed BCG signal by applying energy entropy to the decomposed signal frequency bands. The reconstructed BCG signal can then have enhanced fundamental recurrent patterns without harmonic components and artifact ambiguities. While an embodiment of the disclosure can use energy entropy to reconstruct the decomposed BCG signals, the various embodiments of the disclosure need not be so limited. Other techniques can also be used for reconstructing the decomposed BCG signals.

U.S. patent application Ser. No. 15/168,531 titled "Method and Apparatus for Heart Rate and Respiration Rate Estimation Using Low Power Sensor" filed on May 31, 2016 describes a system and method for decomposing a BCG signal into multiple frequency bands and reconstructing the BCG signal, and is incorporated by reference herein.

At 610, the system may receive filtered-out frequency components from 612, and store the filtered-out frequency components, for example, in memory 210 for further analysis. The present example system may analyze the filtered-out low frequency components to estimate, for example, respiration rate as well as inspiration and expiration onsets. The filtered-out high frequency components may be used, for example, for biometric recognition.

At 616, the present example system may further process the pre-processed signals for signal event segmentation based on, for example, time delay embedding (TDE) beat detection. The TDE approach can produce robust beat locations for different morphological variations of a given signal with low computational cost. The TDE approach maps a signal into a two-dimensional space by plotting sample points against delayed points. Adaptive thresholding beat detection may also be used for signal event segmentation. The U.S. application Ser. No. 15/264,333 filed on Jun. 29, 2016, titled "System and method for Providing a Real-Time Signal Segmentation and Fiducial Points Alignment Framework," describes TDE beat detection and segmentation in more detail. For example, signal event segmentation may be used to identify individual segments in the signals which contain a heartbeat.

At 620, the present example system may process the segmented signals for event locations, which may be heartbeat event locations, and real-time feature alignment may take place at 622 using raw signals (from 608). The process from 616 to 622 is described in more detail in the U.S. patent application Ser. No. 14/928,072 titled "Method for Low-Power-Consumption, Robust Estimation of Cardiovascular Periodicity, Contour Analysis, and Heart Rate" filed on Oct. 30, 2015, where the application describes a system and method for time-delay based beat detection, and is incorporated by reference in its entirety herein. For example, real-time feature alignment may identify one heartbeat location in the signal for each segment in the segmented signal. For example, segments in a segmented, pre-processed signal may be compared with adjacent segments in order to identify correlated points that are considered heartbeat locations.

Various similarity matching techniques may be used for real time feature alignment, such as, for example, a correlation method and/or dynamic time warping (DTW) method. For example, DTW may be used to match temporal similarity patterns of two consecutive clipped segments. The DTW distance provides an indicator of similarity for determining an optimal match between two given sequences.

According to one embodiment, a probability function may be applied to the DTW method to assign greater weights of principal feature points near the middle of a segment and assign lesser weights to edge points that could be interpreted as noise. This may further improve reliability and accuracy of alignment performance. The probability function includes, but is not limited to, a softmax function, entropy, and modulus distance. The U.S. application Ser. No. 15/264,333 filed on Jun. 29, 2016, titled "System and method for Providing a Real-Time Signal Segmentation and Fiducial Points Alignment Framework," describes this process in more detail.

At 624, the present example system may determine the IBI based on the pre-processed signal (e.g., the segmented signals with identified heartbeat locations) and the IBI equation:

$$IBI(i)=beat\_timestamp(i+1)-beat\_timestamp(i)$$

where beat_timestamp is a matrix with the timestamp of all detected beats.

At 626, the present example system may receive the signal and the IBI information, and refine abnormal candidates by performing upon the signal and the IBI information the methods described above (including 1. Channel Combination—Stage 1 screening, 2. Template Matching, 3. Morphological Analysis, and 4. Noise Identification) to perform False Alarm Detection/Masking and get rid of false beat detections at the motion sensor diagnosis stage. In other words, the system determines if the output from 624 contains outliers or artifacts, and refines the output by removing the outliers/artifacts.

At 628, the present example system may use the output from real-time feature alignment of 622 to determine a signal quality confidence indicator, including the signal that has been run through the real-time feature alignment. The alignment level from DTW can be used as confidence indication of signal quality. For example, alignment level may be the ratio of the length of aligned signal to the length of the shorter segment of two pre-aligned signals that are aligned to generate the aligned signal. A higher alignment level indicates that two consecutive segments have higher similarity while a lower alignment level means the signal has larger morphological variation. If the signal quality confidence indicator is below a pre-determined threshold, the process may proceed to 606 for channel selection, and result in re-initialization.

At 630, the present example system outputs the generated refined event locations/fiducial points from the output of the real-time feature alignment (from 622). The refined event locations/fiducial points may be refined BCG IBI.

At 632, the Motion Sensor Anomaly Detection block monitors statistical distribution of abnormal IBIs. Once the value reaches a significant, pre-determined threshold ("Yes") then arrhythmia diagnosis at 718 may occur; this may include sending a notification to the user on the wearable device that arrhythmia has been detected or is highly suspected to have been detected. Alternatively, or in addition, one or more optical sensors may be activated to confirm motion sensor anomaly detection, described in FIG. 7. If the value has not reached a significant threshold ("No") the present example system may continue collecting and processing raw signals from the motion sensor.

Furthermore, at 632, an Nth order median filter may be applied to the Refined BCG IBI from 630. The median filter is described above, and may be used, for example, to distinguish periods of AFib in the signal from other periods.

While an embodiment was described in the flowchart of FIG. 6, it should be understood that various embodiments may use different processes that may show a different flow, add functions, or remove functions.

FIG. 7 is an example flow chart for processing an input signal in accordance with an embodiment of the present disclosure. Referring to FIG. 7, there is shown the flow chart that describes further detecting abnormal candidates in a present example system. The process detailed in FIG. 7 may be a continuation of the process detailed in FIG. 6, which is followed when there is a Motion Sensor Anomaly Detection at 604.

At 706, once an anomaly is detected at 604 from the signal detected by the motion sensor, one or more optical sensors on the user-wearable device will be triggered to detect signals from the user, for example through PPG.

At 708 and 710, the signal from the optical sensor will be processed similarly to 616 and 620 described above, in order to identify heartbeat locations in the signal.

At 712, the present example system determines whether the anomaly detected at 604 is also confirmed by the signal from the optical sensor. If arrhythmia events are confirmed, abnormal PPG and BCG segments will be processed through the compression block and stored in device storage module at 714. The compression block can be implemented to be using—but not limited to—wavelet compression, downsample, etc. In the case that the user is active, the BCG signal can be used for initial screening, and when motion is present or detection confidence is low, the optical sensor will be triggered as primary detection source. If an anomaly event is detected—that is, if both motion and optical sensor confirm arrhythmia symptoms—the system may send a notification to the user recommending that the user then engage in a spot check mode using ECG sensor, for clinical confirmation, at 714. If the optical sensor fails to confirm the anomaly event, then the process may loop back to, for example, the collection of raw signals by the motion sensor.

Whether ECG spot check mode is triggered or not, arrhythmia diagnosis may occur at 718, where the user may be notified by the display on the wearable device of positive arrhythmia detection.

Figure 8:
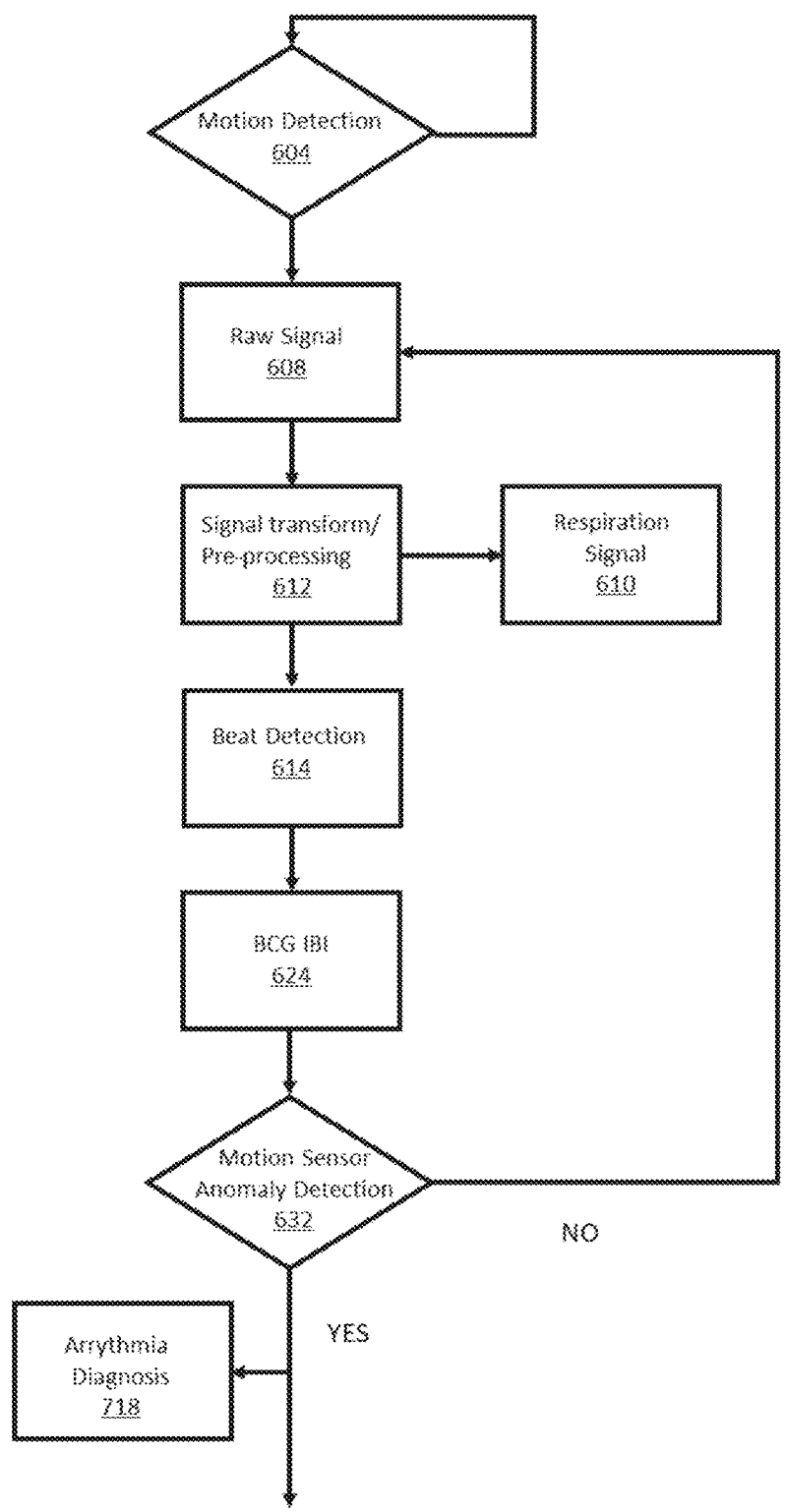
FIG. 8 depicts an arrhythmia triage flowchart according to an embodiment of the present inventive concept.
Figure 9:
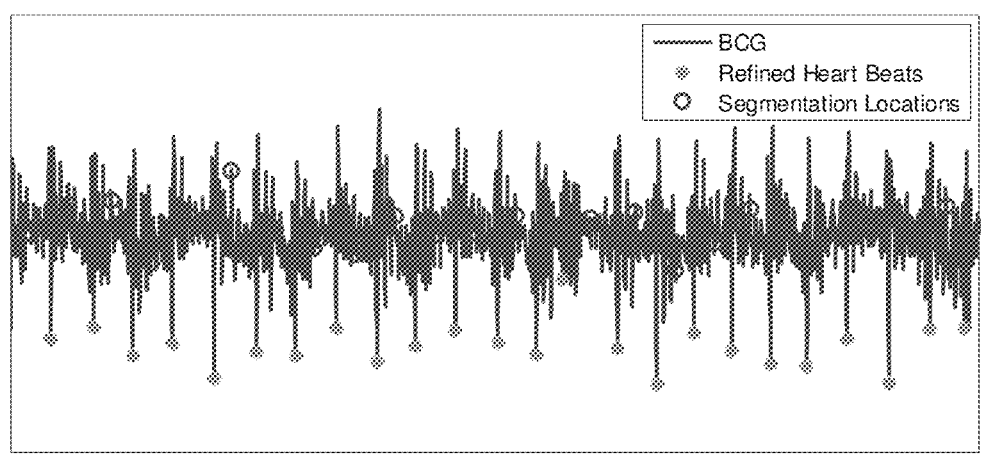
FIG. 9 depicts BCG with segmentation locations and refined beats according to an embodiment of the present inventive concept.

FIG. 8 is an example flow chart for processing an input signal in accordance with another embodiment of the present disclosure. Referring to FIG. 8, there is shown the flow chart that describes detecting abnormal candidates in a present example system, which is similar to the flow chart shown in FIG. 6, except with some of the steps removed or skipped.

The signal to be processed may be received from a wearable device such as, for example, a user-wearable device 100. The user-wearable device 100 may detect the biosignals via the sensor module 120. As described below, the steps illustrated in FIG. 8 are similar to the same-numbered steps illustrated in FIG. 6, except that the steps illustrated in FIG. 8 may have different inputs based upon which steps are skipped, and may send their outputs to different steps based on which steps are skipped, as described below.

In FIG. 8, motion is detected 604, generating, for example, a BCG raw signal at 608 without going through channel selection. The raw signal is pre-processed at 612, and the filtered-out frequency components are stored in, for example memory 210 for further analysis. Beat detection is performed on the pre-processed signal at 614. Beat detection may comprise any combination of one or more of 616, 620, and 622 described above in reference to FIG. 6. At 624, the system may determine IBI, then send the output for Motion sensor Anomaly Detection at 632. At 632, the Motion Sensor Anomaly Detection block monitors statistical distribution of abnormal IBIs. Once the value reaches a significant, pre-determined threshold ("Yes") then arrhythmia diagnosis at 718 may occur; this may include sending a notification to the user on the wearable device that arrhythmia has been detected or is highly suspected to have been detected. Alternatively, or in addition, one or more optical sensors may be activated to confirm motion sensor anomaly detection, described in FIG. 7. If the value has not reached a significant threshold ("No") the present example system may continue collecting and processing raw signals from the motion sensor.

The terminology used here is for the purpose of describing particular embodiments only and is not intended to limit the disclosure. In the drawings, the thickness, width, length, size, etc., of layers, areas, regions, components, elements, etc., may be exaggerated for clarity. Like reference numerals refer to like elements throughout.

As utilized herein, "and/or" means any one or more of the items in the list joined by "and/or." As an example, "x and/or y" means any element of the three-element set {(x), (y), (x, y)}. In other words, "x and/or y" means "one or both of x and y". As another example, "x, y, and/or z" means any element of the seven-element set {(x), (y), (z), (x, y), (x, z), (y, z), (x, y, z)}. In other words, "x, y, and/or z" means "one or more of x, y, and z". As utilized herein, the term "exemplary" means serving as a non-limiting example, instance, or illustration. As utilized herein, the terms "e.g." and "for example" set off lists of one or more non-limiting examples, instances, or illustrations.

Also, the singular forms are intended to include the plural forms as well, unless the context clearly indicates otherwise. It will be further understood that the terms "comprises," "comprising," "includes," and/or "including," when used in this specification, specify the presence of stated features, numbers, steps, operations, elements, and/or components, but do not preclude the presence or addition of one or more other features, numbers, steps, operations, elements, components, and/or groups thereof.

In addition, it will be understood that when an element A is referred to as being "connected to" or "coupled to" an element B, the element A can be directly connected to or coupled to the element B, or an intervening element C may be present between the elements A and B so that the element A can be indirectly connected to or coupled to the element B.

Furthermore, although the terms first, second, etc., may be used to describe various members, elements, regions, layers and/or sections, these members, elements, regions, layers and/or sections should not be limited by these terms. These terms are only used to distinguish one member, element, region, layer, and/or section from another. Thus, for example, a first member, a first element, a first region, a first layer, and/or a first section discussed below could be termed a second member, a second element, a second region, a second layer, and/or a second section without departing from the teachings of the present disclosure.

Spatially relative terms, such as "upper," "lower," "side," and the like, may be used for ease of description to describe the relationship of one element or feature to another element(s) or feature(s) as illustrated in the figures. It will be understood that the spatially relative terms are intended to encompass different orientations of the device in use or operation in addition to the orientation depicted in the figures. For example, if the device in the figures is turned upside-down, elements described as "below" or "beneath" other elements or features would then be oriented "above" the other elements or features. Thus, the term "below" can encompass both an orientation of above and below.

Furthermore, a term such as a "module," "block," etc., may comprise hardware and/or software components, and may further comprise other modules/blocks/etc., as well as be a part of a larger module or a block. Generally, the terms "module" and "block" may be interchangeable.

While various embodiments of the disclosure have been described above, it should be understood that they have been presented as non-limiting examples only. While the foregoing has been described with reference to certain aspects and examples, it will be understood by those skilled in the art that various changes may be made and equivalents may be substituted without departing from the scope of the disclosure. In addition, many modifications may be made to adapt a particular situation or material to the teachings of the disclosure without departing from its scope. Therefore, it is intended that the disclosure not be limited to the particular example(s) disclosed, but that the disclosure will include all examples falling within the scope of the appended claims.

What is claimed is:

1. A method for detecting arrhythmia, comprising:
   receiving, via at least one motion sensor, channels of raw motion signals for a user;
   monitoring the channels for motion activity;
   generating segments from the raw motion signals;
   determining heartbeat event locations from the generated segments; and
   performing false alarm detection on the raw motion signals and the heartbeat event locations to generate refined abnormal candidates.

2. The method of claim 1, further comprising:
   before generating segments from the raw motion signals, monitoring an activity level of the user to determine whether the user is stationary based on whether the activity level of the user is below a predetermined threshold.

3. The method of claim 1, wherein the at least one motion sensor of includes a three-axis accelerometer, and the channels comprise three channels each respectively corresponding to one of three-axes of the three-axis accelerometer, and the raw motion signals are ballistocardiogram (BCG) signals.

4. The method of claim 3, wherein the at least one motion sensor consists of one motion sensor.

5. The method of claim 1, further comprising:
   determining an inter-heat interval (IBI) of each of the channels.

6. The method of claim 5, wherein performing false alarm detection further comprises:
  detecting, from the heartbeat event locations, a first abnormal candidate;
  determining, based on different change trends of the IBI for at least two of the channels, that the first abnormal candidate is a low confidence abnormal candidate;
  detecting, from the heartbeat event locations, at least one second abnormal candidate; and
  determining, by matching the first abnormal candidate and the at least one second abnormal candidate such that a predetermined threshold of matching has been met, that the first abnormal candidate and the at least one second abnormal candidate are high confidence abnormal candidates.

7. The method of claim 6, wherein the generated refined abnormal candidates comprise the first abnormal candidate.

8. The method of claim 6, wherein performing false alarm detection further comprises masking noise on the first abnormal candidate by excluding snoring motions from the first abnormal candidate to generate a masked first abnormal candidate, and
  wherein the generated refined abnormal candidates comprise the masked first abnormal candidate.

9. The method of claim 6, further comprising:
  receiving, via at least one optical sensor, second raw motion signals of the user;
  generating second segments from the second raw motion signals;
  determining second heartbeat event locations from the generated second segments; and
  determining, by matching the second raw motion signals and the raw motion signals, a positive arrhythmia detection.

10. The method of claim 9, further comprising:
  displaying a notification notifying the user of the positive arrhythmia detection and recommendation to the user to trigger an electrocardiogram (ECG) spot check.

11. The method of claim 1, further comprising:
  determining, based on the heartbeat event locations, onset and offset arrhythmia events; and
  calculating, based on the onset and offset arrhythmia events, atrial fibrillation burden of the user.

12. The method of claim 1, further comprising:
  applying an Nth order median filter to the generated refined abnormal candidates, where N is a natural number.

13. A method for detecting arrhythmia, comprising:
  receiving, via at least one motion sensor, raw motion signals for a user;
  monitoring the raw motion signals for motion activity;
  pre-processing the raw motion signals to filter out components of the raw motion signals;
  storing the filtered out components; and
  determining an inter-beat interval (IBI) of the raw motion signals.

14. An electronic device, comprising:
  at least one motion sensor configured to detect raw motion signals for a user and output the raw motion signals as individual channels;
  a processor configured to:
    monitor the channels for motion activity;
    generate segments from the raw motion signals;
    determine heartbeat event locations from the generated segments; and
    perform false alarm detection on the raw motion signals and the heartbeat event locations to generate refined abnormal candidates; and
  a display configured to display at least one of the one or more health information.

15. The electronic device of claim 14, wherein the processor is further configured to:
  before generating segments from the raw motion signals, monitor an activity level of the user to determine whether the user is stationary based on whether the activity level of the user is below a predetermined threshold.

16. The electronic device of claim 14, wherein the at least one motion sensor includes a three-axis accelerometer, and the channels comprise three channels each respectively corresponding to one of three-axes of the three-axis accelerometer, and the raw motion signals are ballistocardiogram (BCG) signals.

17. The electronic device of claim 14, further comprising a transform module configured to transform the raw motion signals to reconstructed signals, wherein the transform module comprises:
  a decomposing module configured to decompose the raw motion signals to decomposed signals, and
  a reconstruction module configured to reconstruct the decomposed signals to the reconstructed signals.

18. The electronic device of claim 14, wherein the processor is further configured to:
  determine an inter-beat interval (IBI) of each of the channels; and
  wherein the processor is further configured to:
  detect, from the heartbeat event locations, a first abnormal candidate;
  determine, based on different change trends of the IBI for at least two of the channels, that the first abnormal candidate is a low confidence abnormal candidate;
  detect, from the heartbeat event locations, at least one second abnormal candidate; and
  determine, by matching the first abnormal candidate and the at least one second abnormal candidate such that a predetermined threshold of matching has been met, that the first abnormal candidate and the at least one second abnormal candidate are high confidence abnormal candidates.

19. The electronic device of claim 18, wherein the generated refined abnormal candidates comprise the first abnormal candidate.

20. The electronic device of claim 18, wherein the processor is further configured to mask noise on the first abnormal candidate by excluding snoring motions from the first abnormal candidate to generate a masked first abnormal candidate; and
  wherein the generated refined abnormal candidates comprise the masked first abnormal candidate.

21. The electronic device of claim 18, further comprising at least one optical sensor configured to detect second raw motion signals of the user,
  wherein the processor is further configured to:
    receive second raw motion signals of the user;
    generate second segments from the second raw motion signals;
    determine second heartbeat event locations from the generated second segments; and
    determine, by matching the second raw motion signals and the raw motion signals, a positive arrhythmia detection.

22. The electronic device of claim 21,
wherein the display is further configured to display a notification to the user of the positive arrhythmia detection and recommendation to the user to trigger an electrocardiogram (ECG) spot check.

\* \* \* \* \*